(12) United States Patent
Shimamura et al.

(10) Patent No.: US 11,484,221 B2
(45) Date of Patent: Nov. 1, 2022

(54) DYNAMIC ANALYSIS APPARATUS, DYNAMIC ANALYSIS SYSTEM, EXPECTED RATE CALCULATION METHOD, AND RECORDING MEDIUM

(71) Applicant: Konica Minolta, Inc., Tokyo (JP)

(72) Inventors: Kenta Shimamura, Hino (JP); Noritsugu Matsutani, Musashino (JP); Jun Hanaoka, Otsu (JP)

(73) Assignee: KONICA MINOLTA, INC., Tokyo (JP)

( * ) Notice: Subject to any disclaimer, the term of this patent is extended or adjusted under 35 U.S.C. 154(b) by 365 days.

(21) Appl. No.: 16/804,742

(22) Filed: Feb. 28, 2020

(65) Prior Publication Data

US 2020/0297240 A1    Sep. 24, 2020

(30) Foreign Application Priority Data

Mar. 20, 2019 (JP) .............................. JP2019-053096

(51) Int. Cl.
| | |
|---|---|
| *A61B 5/08* | (2006.01) |
| *A61B 5/026* | (2006.01) |
| *A61B 5/00* | (2006.01) |
| *G06T 7/00* | (2017.01) |
| *A61B 6/00* | (2006.01) |

(52) U.S. Cl.
CPC ............. *A61B 5/08* (2013.01); *A61B 5/004* (2013.01); *A61B 5/026* (2013.01); *A61B 6/5205* (2013.01); *G06T 7/0014* (2013.01); *G06T 2207/30061* (2013.01); *G06T 2207/30096* (2013.01)

(58) Field of Classification Search
None
See application file for complete search history.

(56) References Cited

U.S. PATENT DOCUMENTS

| 10,149,658 B2 * | 12/2018 | Tsunomori ............. A61B 6/463 |
| 2014/0219416 A1 * | 8/2014 | Kimoto ................ A61B 6/5205 |
| | | 382/131 |

(Continued)

FOREIGN PATENT DOCUMENTS

| JP | 2016214725 A | * 12/2016 | ............. G06T 5/008 |
| JP | 2016214725 A |   12/2016 | |
| JP | 2018000926 A | *  1/2018 | ........... G06T 11/206 |

*Primary Examiner* — Gandhi Thirugnanam
(74) *Attorney, Agent, or Firm* — Lucas & Mercanti, LLP

(57) ABSTRACT

Provided is a dynamic analysis apparatus that predicts a respiratory function value based on frame images showing dynamics of chest. The dynamic analysis apparatus includes a hardware processor that obtains a first lung size value of a removal target site and a second lung size value of a left or right lung field including the removal target site, calculates a proportion between the first and second lung size values as a size proportion, calculates a first feature amount concerning respiratory function of the left or right lung field including the removal target site and a second feature amount concerning respiratory function of the lung fields as a whole, calculates a proportion between the first and second feature amounts as a feature amount proportion, and calculates an expected rate of the respiratory function without the removal target site, based on a product of the size proportion and the feature amount proportion.

10 Claims, 5 Drawing Sheets

(56) References Cited

U.S. PATENT DOCUMENTS

| | | | |
|---|---|---|---|
| 2015/0005659 A1* | 1/2015 | Masumoto | A61B 6/5217 |
| | | | 600/538 |
| 2017/0091930 A1* | 3/2017 | Kozuka | G16H 30/40 |
| 2017/0323440 A1* | 11/2017 | Tsunomori | G16H 50/30 |
| 2017/0325771 A1* | 11/2017 | Tsunomori | G06T 7/0016 |
| 2018/0005374 A1* | 1/2018 | Kasai | G06T 7/0016 |
| 2018/0342056 A1* | 11/2018 | Matsutani | G06T 7/12 |
| 2020/0297240 A1* | 9/2020 | Shimamura | G06T 7/0014 |
| 2020/0327665 A1* | 10/2020 | Shimamura | A61B 6/541 |
| 2021/0304896 A1* | 9/2021 | Chen | G16H 40/67 |

* cited by examiner

| ANATOMICAL UNIT | LUNG SIZE VALUE |
|---|---|
| RIGHT LUNG | 10 |
| LEFT LUNG | 9 |
| RIGHT SUPERIOR LOBE | 3 |
| MIDDLE LOBE | 2 |
| RIGHT INFERIOR LOBE | 5 |
| ⋮ | ⋮ |

DYNAMIC ANALYSIS APPARATUS, DYNAMIC ANALYSIS SYSTEM, EXPECTED RATE CALCULATION METHOD, AND RECORDING MEDIUM

CROSS-REFERENCE TO RELATED APPLICATIONS

The entire disclosure of Japanese Patent Application No. 2019-053096, filed on Mar. 20, 2019, including description, claims, drawings and abstract is incorporated herein by reference in its entirety.

BACKGROUND

Technological Field

The present invention relates to a dynamic analysis apparatus, a dynamic analysis system, an expected rate calculation method, and a recording medium.

Description of the Related Art

More than 30,000 patients undergo lung cancer surgery annually in Japan. Though its mortality rate has been decreasing these years, lung cancer surgery is still accompanied by high risk of complications. Facing indications for lung cancer surgery, doctors consider risk assessment values according to the guideline and various other factors so as to comprehensively predict risk and determine plans of the surgery, including appropriateness of surgery, possibility of limited surgery, and the like. One of the important factors of such risk assessment is prediction of the respiratory function after surgery. The respiratory function after surgery does not only affect the risk assessment results according to the guideline but also is strongly associated to complications. It is important to have access to accurate information in this respect.

Though pharmacological therapies may be an option for lung cancer treatment, excision is effective in view of permanent cure, and it is desirable to excise lung cancer by surgery if possible. An entire left or right lung is excised in pulmonary excision surgery in some cases, but lobectomy is more common. A pulmonary segment, which is a segment smaller than a lobe, may be excised in order to keep the lung after surgery as large as possible. Such excision is called limited surgery. However, cancer might have spread to surrounding pulmonary segments before limited surgery, and it is desirable to excise a lobe in view of permanent cure. One of the criteria for determining whether or not surgery, or limited surgery is to be performed is based on prediction of the respiratory function after surgery. In some cases where the expected rate of the respiratory function after surgery is under a predetermined threshold value, limited surgery is indicated or surgery is not performed at all even for patients aiming for permanent cure because of high risk of complications and the like. Improvements in the accuracy of prediction of the respiratory function after surgery can increase the accuracy of assessment of risk after surgery. Thus, in the case where the risk after surgery is assessed to be low, lobectomy may be selected for permanent cure, instead of segmental excision. In the case where the risk after surgery is assessed to be high, it is possible to accurately determine that limited surgery is to be performed or that surgery is not to be performed for risk reduction.

One of the methods for predicting the respiratory function after surgery is a pulmonary blood flow scintigraphy test. However, the pulmonary blood flow scintigraphy test requires a huge and expensive test equipment. Only hospitals comparatively large can own such an equipment, and otherwise it cannot be used. Even in a medical facility with a scintigraphy test equipment, patients usually have to be on a one-week waiting list for a scintigraphy test after ordering because of necessity for management of radioisotopes, and are subject to large exposure. Thus, only patients with high risk undergo a scintigraphy test. Risk of complications is not accurately comprehended in many cases because of this problem. The pulmonary blood flow scintigraphy test gives images of only blood flow of the left and right lungs and does not locate the lungs. Thus, it is difficult to accurately predict the respiratory function.

To solve such problems, a technique to predict the respiratory function after surgery using an X-ray dynamic image (s) is disclosed in Patent Document 1 (JP2016-214725A), for example. Specifically, the respiratory function value after surgery is predicted in Patent Document 1 as follows: a region corresponding to the range of lung excision is selected by the user via the operation interface or the like; a feature amount of the lung field without the selected region is calculated; a feature amount of the entire lung field is calculated; a ratio between the feature amount of the lung field without the selected region and that of the entire lung field is calculated; and a test result of a spirometry test is multiplied by the said ratio.

SUMMARY

However, as it is necessary to designate the removal target region of excision on the dynamic image(s) in the technique disclosed in Patent Document 1, the three-dimensional range to be removed cannot be accurately designated on the two-dimensional dynamic image(s). Thus, the feature amount of the respiratory function cannot be accurately predicted.

An object of the present invention is to accurately predict the respiratory function value after excision of part of the lung on the dynamic image(s) of the chest.

To achieve at least one of the abovementioned objects, a dynamic analysis apparatus reflecting one aspect of the present invention predicts a respiratory function value of a subject based on a plurality of frame images showing dynamics of a chest of the subject. The dynamic analysis apparatus includes a hardware processor that:

obtains a first lung size value of a removal target site and a second lung size value of a left or right lung field that includes the removal target site, in lung fields of the subject;

calculates a proportion between the first lung size value of the removal target site and the second lung size value of the left or right lung field that includes the removal target site, as a size proportion;

calculates a first feature amount concerning respiratory function of the left or right lung field that includes the removal target site and a second feature amount concerning respiratory function of the lung fields as a whole, based on the plurality of frame images;

calculates a proportion between the first feature amount concerning the respiratory function of the left or right lung field that includes the removal target site and the second feature amount concerning the respiratory function of the lung fields as a whole, as a feature amount proportion; and calculates an expected rate of the respiratory function after the removal target site is removed from the lung fields, based on a product of the calculated size proportion and the calculated feature amount proportion.

To achieve at least one of the abovementioned objects, an expected rate calculation method for a dynamic analysis apparatus reflecting another aspect of the present invention predicts a respiratory function value of a subject based on a plurality of frame images showing dynamics of a chest of the subject. The expected rate calculation method includes:

obtaining a first lung size value of a removal target site and a second lung size value of a left or right lung field that includes the removal target site, in lung fields of the subject;

calculating a proportion between the first lung size value of the removal target site and the second lung size value of the left or right lung field that includes the removal target site, as a size proportion;

calculating a first feature amount concerning respiratory function of the left or right lung field that includes the removal target site and a second feature amount concerning respiratory function of the lung fields as a whole, based on the plurality of frame images;

calculating a proportion between the first feature amount concerning the respiratory function of the left or right lung field that includes the removal target site and the second feature amount concerning the respiratory function of the lung fields as a whole, as a feature amount proportion; and calculating an expected rate of the respiratory function after the removal target site is removed from the lung fields, based on a product of the calculated size proportion and the calculated feature amount proportion.

To achieve at least one of the abovementioned objects, a non-transitory recording medium storing a computer-readable program reflecting another aspect of the present invention causes a computer used for a dynamic analysis apparatus that predicts a respiratory function value of a subject based on a plurality of frame images showing dynamics of a chest of the subject:

to obtain a first lung size value of a removal target site and a second lung size value of a left or right lung field that includes the removal target site, in lung fields of the subject;

to calculate a proportion between the first lung size value of the removal target site and the second lung size value of the left or right lung field that includes the removal target site, as a size proportion;

to calculate a first feature amount concerning respiratory function of the left or right lung field that includes the removal target site and a second feature amount concerning respiratory function of the lung fields as a whole, based on the plurality of frame images;

to calculate a proportion between the first feature amount concerning the respiratory function of the left or right lung field that includes the removal target site and the second feature amount concerning the respiratory function of the lung fields as a whole, as a feature amount proportion; and to calculate an expected rate of the respiratory function after the removal target site is removed from the lung fields, based on a product of the calculated size proportion and the calculated feature amount proportion.

BRIEF DESCRIPTION OF THE DRAWINGS

The advantages and features provided by one or more embodiments of the invention will become more fully understood from the detailed description given hereinbelow and the appended drawings which are given by way of illustration only, and thus are no intended as a definition of the limits of the present invention, wherein.

DETAILED DESCRIPTION OF THE EMBODIMENTS

Hereinafter, a dynamic analysis apparatus, a dynamic analysis system, an expected rate calculation method, and a recording medium according to the present invention are described with reference to the drawings. However, the scope of the invention is not limited to the disclosed embodiments.

[Configuration of Dynamic Analysis System 100]

First, a configuration of the present embodiment is described.

Figure 1:
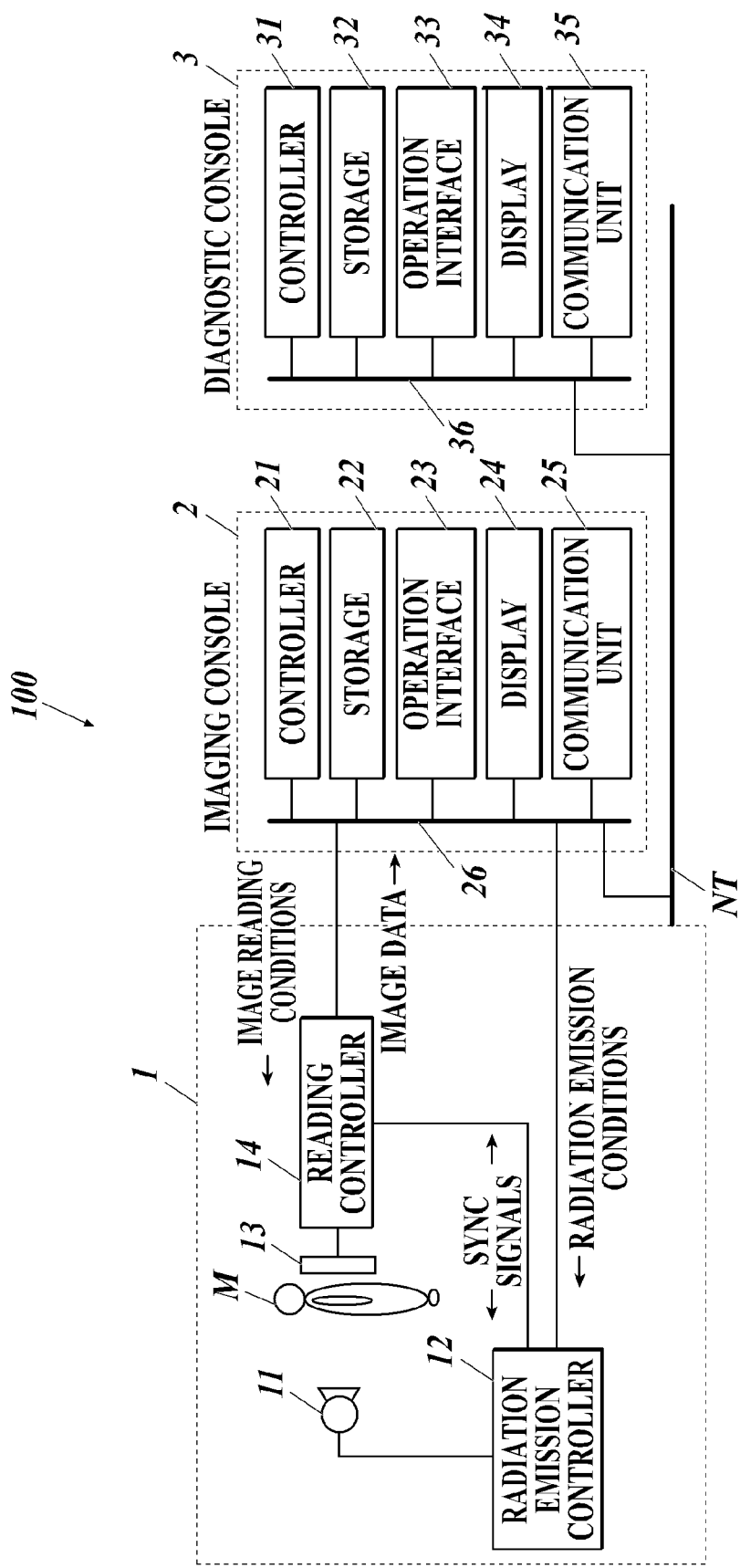
FIG. 1 shows an overall configuration of a dynamic analysis system according to an embodiment of the present invention.

FIG. 1 shows an overall configuration of a dynamic analysis system 100 according to the present embodiment.

As shown in FIG. 1, the dynamic analysis system 100 includes: an imaging apparatus 1; an imaging console 2 connected with the imaging apparatus 1 via a communication cable or the like; and a diagnostic console 3 connected with the imaging console 2 via a communication network NT, such as a local area network (LAN). These components of the dynamic analysis system 100 are in conformity with DICOM (Digital Image and Communications in Medicine) standard and communicate with one another in conformity with DICOM.

[Configuration of Imaging Apparatus 1]

The imaging apparatus 1 is an imaging apparatus that images a cyclic dynamic state of the chest of a subject, for example. Examples of the cyclic dynamic state thereof include: change in shape of the lungs by expansion and contraction of the lungs with respiration; and pulsation of the heart. Dynamic imaging (kinetic imaging) is performed by repeatedly emitting pulsed radiation, such as pulsed X-rays, to a subject at predetermined time intervals (pulse emission) or continuously emitting radiation without a break to a subject at a low dose rate (continuous emission), thereby obtaining a plurality of images showing the dynamic state.

A series of images obtained by dynamic imaging is called a dynamic image Images constituting a dynamic image are called frame images. In the embodiments described hereinafter, dynamic imaging of the chest front is performed by pulse emission as an example.

A radiation source 11 is disposed to face a radiation detector 13 with a subject M in between, and emits radiation (X-rays) to the subject under the control of a radiation emission controller 12.

The radiation emission controller 12 is connected with the imaging console 2, and controls the radiation source 11 on the basis of radiation emission conditions input from the imaging console 2 so as to perform radiographic imaging. The radiation emission conditions input from the imaging console 2 include a pulse rate, a pulse width, a pulse interval, the number of frames (frame images) to be taken by one imaging, a value of current of an X-ray tube, a value of voltage of the X-ray tube, and a type of added filter. The pulse rate is the number of times radiation is emitted per second, and matches the frame rate described below. The pulse width is a period of time for one radiation emission. The pulse interval is a period of time from the start of one radiation emission to the start of the next radiation emission, and matches the frame interval described below.

The radiation detector 13 includes a semiconductor image sensor such as a flat panel detector (FPD).

The FPD is constituted of detection elements (pixels) arranged at predetermined points on a substrate, such as a glass substrate, in a matrix. The detection elements detect radiation (intensity of radiation) that has been emitted from the radiation source 11 and passed through at least a subject M, convert the detected radiation into electric signals, and accumulate the electric signals therein. The pixels are provided with switches, such as thin film transistors (TFTs). There are an indirect conversion type FPD that converts X-rays into electric signals with photoelectric conversion element(s) via scintillator(s) and a direct conversion type FPD that directly converts X-rays into electric signals. Either of them can be used.

The radiation detector 13 is disposed to face the radiation source 11 having a subject M in between.

A reading controller 14 is connected with the imaging console 2. The reading controller 14 controls the switches of the pixels of the radiation detector 13 on the basis of image reading conditions input from the imaging console 2 to switch the pixels to read the electric signals accumulated in the pixels, thereby reading the electric signals accumulated in the radiation detector 13 and obtaining image data. This image data is a frame image(s). The reading controller 14 outputs the obtained frame images to the imaging console 2. The image reading conditions include a frame rate, a frame interval, a pixel size, and an image size (matrix size). The frame rate is the number of frame images to be obtained per second, and matches the pulse rate described above. The frame interval is a period of time from the start of one frame image obtaining action to the start of the next frame image obtaining action, and matches the pulse interval described above.

The radiation emission controller 12 and the reading controller 14 are connected to each other, and exchange sync signals so as to synchronize radiation emission actions with image reading actions.

[Configuration of Imaging Console 2]

The imaging console 2 outputs the radiation emission conditions and the image reading conditions to the imaging apparatus 1 so as to control the radiographic imaging and the radiographic image reading actions performed by the imaging apparatus 1, and also displays the dynamic image obtained by the imaging apparatus 1 so that a radiographer, such as a radiologist, can check if positioning has no problem, and also can determine if the dynamic image is suitable for diagnosis.

The imaging console 2 includes, as shown in FIG. 1, a controller 21, a storage 22, an operation interface 23, a display 24 and a communication unit 25. These components are connected to one another via a bus 26.

The controller 21 includes a CPU (Central Processing Unit) and a RAM (Random Access Memory). The CPU of the controller 21 reads a system program and various process programs stored in the storage 22 in response to operation on the operation interface 23, opens the read programs in the RAM, and performs various processes, such as the below-described imaging control process, in accordance with the opened programs, thereby performing concentrated control of actions of the components of the imaging console 2 and the radiation emission actions and the reading actions of the imaging apparatus 1.

The storage 22 is constituted of a non-volatile semiconductor memory, a hard disk or the like. The storage 22 stores therein various programs to be executed by the controller 21, parameters necessary to perform processes of the programs, data, such as process results, and the like. For example, the storage 22 stores therein a program for the imaging control process shown in FIG. 2. The storage 22 also stores therein the radiation emission conditions and the image reading conditions correlated with examination target parts and imaging directions. The programs are stored in the form of computer readable program code, and the controller 21 acts in accordance with the program code.

The operation interface 23 includes: a keyboard including cursor keys, number input keys and various function keys; and a pointing device, such as a mouse, and outputs, to the controller 21, command signals input by key operation on the keyboard or by mouse operation. The operation interface 23 may have a touchscreen on the display screen of the display 24. In this case, the operation interface 23 outputs command signals input via the touchscreen to the controller 21.

The display 24 is constituted of a monitor, such as an LCD (Liquid Crystal Display) or a CRT (Cathode Ray Tube), and displays thereon commands input from the operation interface 23, data and the like in accordance with commands of display signals input from the controller 21.

The communication unit 25 includes a LAN adapter, a modem and a terminal adapter (TA), and controls data exchange with devices connected to the communication network NT.

[Configuration of Diagnostic Console 3]

The diagnostic console 3 is a device which obtains the dynamic image from the imaging console 2, and predicts the respiratory function after the pulmonary excision surgery in which part of the lung is removed by excision based on the obtained dynamic image.

The diagnostic console 3 includes, as shown in FIG. 1, a controller 31 (hardware processor), a storage 32, an operation interface 33, a display 34 and a communication unit 35. These components are connected to one another via a bus 36.

The controller 31 includes a CPU and a RAM. The CPU of the controller 31 reads a system program and various process programs stored in the storage 32 in response to operations through the operation interface 33, opens the read programs in the RAM, and performs various processes, such as the below-described respiratory function prediction process, in accordance with the opened programs, thereby performing concentrated control of actions of the units or the like of the diagnostic console 3.

The storage 32 is constituted of a nonvolatile semiconductor memory, a hard disk or the like. The storage 32 stores therein various programs, including a program for the respiratory function prediction process, to be executed by the controller 31, parameters necessary to perform processes of the programs, data, such as process results, and the like. The programs are stored in the form of a computer readable program code(s), and the controller 31 acts in accordance with the program code.

The storage 32 stores dynamic images taken in the past and prediction results of respiratory function values after surgery in association with patient information (e.g., patient ID, patient name, height, weight, age, sex, etc.), and examination information (e.g., examination ID, examination date, examination target part (here, chest), and imaging direction (frontal, lateral)).

Figures 4, 5:
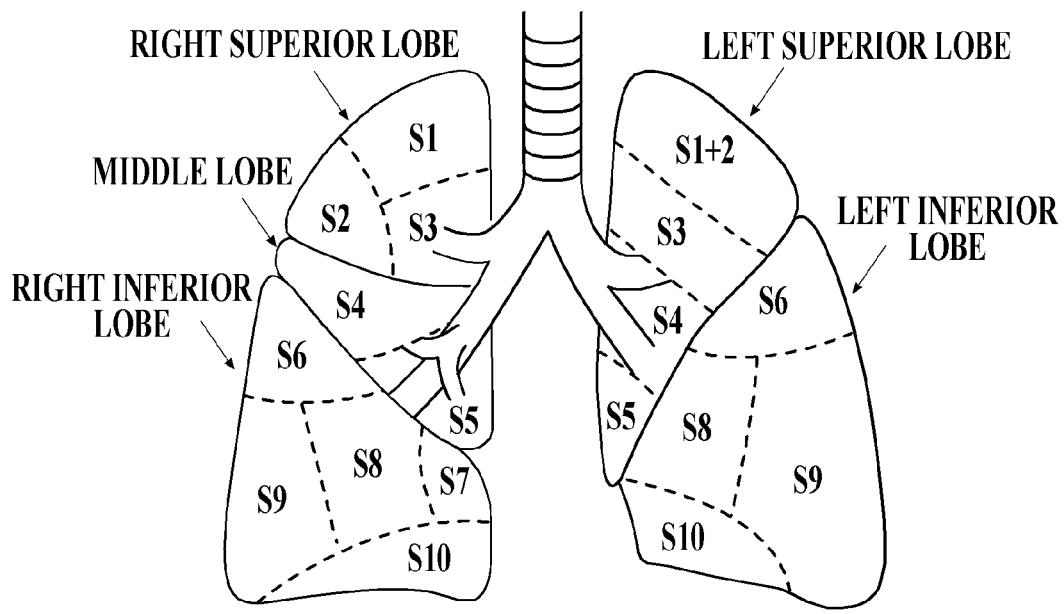
FIG. 4 shows anatomical units of the lungs.
FIG. 5 is an example of a table of lung size values.

The storage 32 also stores a table of lung size values 321 (see FIG. 5). The table of lug size 321 is a table recording the lung size values for respective anatomical units of the lungs. It is described in detail later.

The operation interface 33 includes: a keyboard including cursor keys, number input keys and various function keys; and a pointing device, such as a mouse, and outputs, to the controller 31, command signals input with key operation by the user on the keyboard or by mouse operation. The operation interface 33 may have a touchscreen on the display screen of the display 34. In this case, the operation interface 33 outputs command signals input via the touchscreen to the controller 31.

The display 34 is constituted of a monitor, such as an LCD or a CRT, and performs various types of display in accordance with commands of display signals input from the controller 31.

The communication unit 35 includes a LAN adapter, a modem and a TA, and controls data exchange with devices connected to the communication network NT.

[Actions of Dynamic Analysis System 100]

Next, actions of the dynamic analysis system 100 according to the embodiment(s) are described.

(Actions of Imaging Apparatus 1 and Imaging Console 2)

First, imaging actions performed by the imaging apparatus 1 and the imaging console 2 are described.

Figure 2:
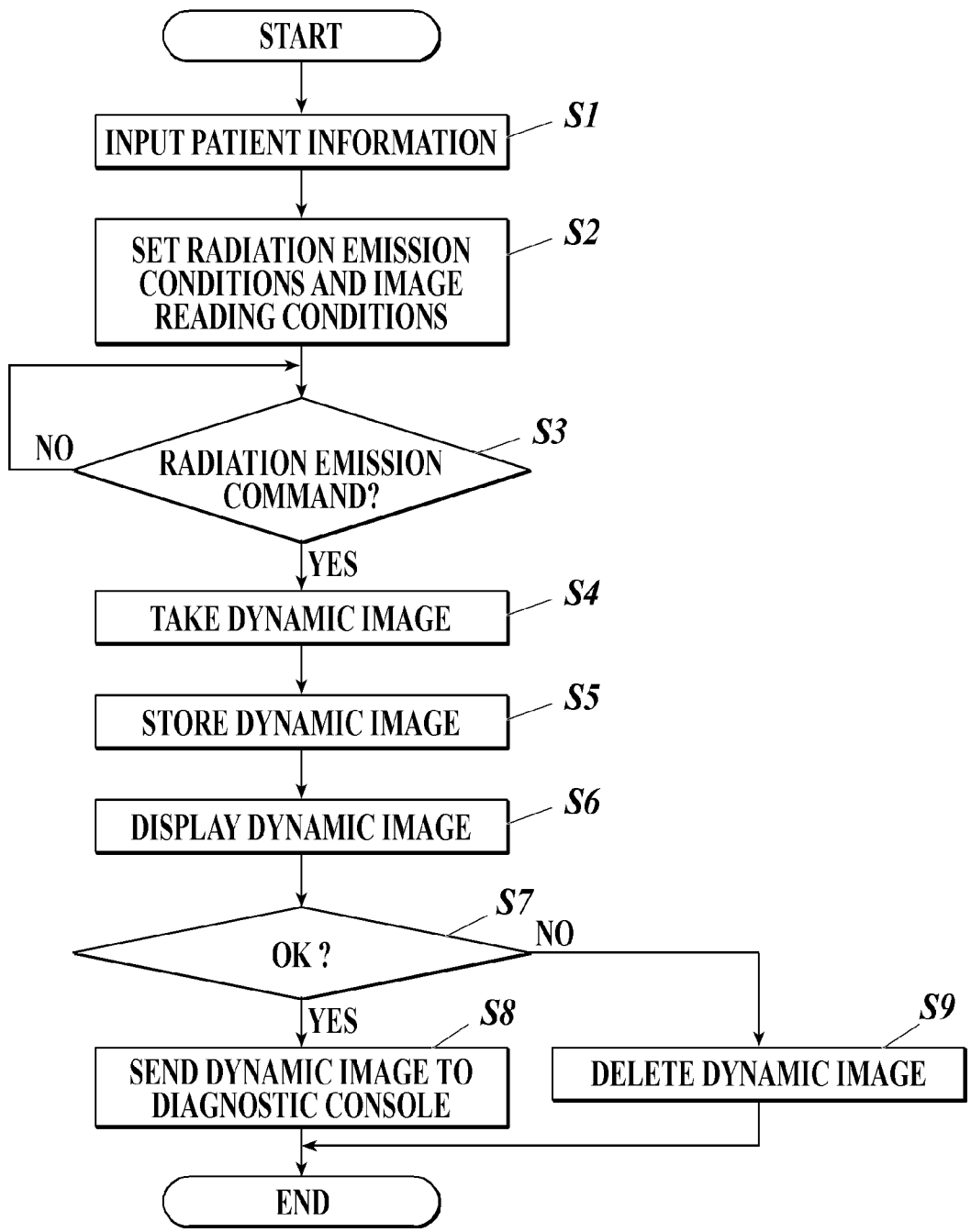
FIG. 2 is a flowchart of imaging control process performed by a controller of an imaging console in FIG. 1.

FIG. 2 shows the imaging control process performed by the controller 21 of the imaging console 2. The imaging control process is executed by the controller 21 in coordination with the program stored in the storage 22.

First, the radiographer operates the operation interface 23 of the imaging console 2 to input the patient information of the subject M, and the examination information (Step S1).

Next, the controller 21 reads the radiation emission conditions from the storage 22 so as to set them in the radiation emission controller 12, and also reads the image reading conditions from the storage 22 so as to set them in the reading controller 14 (Step S2).

Next, the controller 21 waits for a radiation emission command to be input via the operation interface 23 (Step S3). Here, the radiographer places the subject M between the radiation source 11 and the radiation detector 13 and performs positioning. When preparations for imaging are complete, the radiographer operates the operation interface 23 so as to input the radiation emission command.

In receipt of the radiation emission command input through the operation interface 23 (Step S3; YES), the controller 21 outputs an imaging start command to the radiation emission controller 12 and the reading controller 14 to start dynamic imaging (Step S4). That is, the radiation source 11 emits radiation at pulse intervals set in the radiation emission controller 12, and accordingly the radiation detector 13 obtains (generates) a series of frame images. During the dynamic imaging, the radiographer directs a respiratory guidance or an instruction of holding breath, such as "breathe in", "breathe out", or "hold breath". The imaging device 1 may include a sound output unit and/or a display, and when the controller 21 outputs the imaging start command, the sound output unit and/or the display may output a sound and/or display of an indication of a respiratory guidance or an instruction of holding breath, such as "breathe in", "breathe out" or "hold breath".

In receipt of the radiation emission ending command input via the operation interface 23, the controller 21 outputs an imaging end command to the radiation emission controller 12 and the reading controller 14 to stop the imaging actions.

The frame images obtained by imaging are successively input to the imaging console 2 and stored in the storage 22, the frame images being correlated with respective numbers indicating what number in the imaging order the respective frame images have been taken (frame number) (Step S5), and also displayed on the display 24 (Step S6). The radiographer checks the positioning or the like with the displayed dynamic image, and determines whether the dynamic image obtained by dynamic imaging is suitable for diagnosis (Imaging OK) or re-imaging is necessary (Imaging NG). Then, the radiographer operates the operation interface 23 so as to input the determination result.

When the determination result "Imaging OK" is input by the radiographer performing a predetermined operation on the operation interface 23 (Step S7; YES), the controller 21 attaches, to the respective frame images obtained by dynamic imaging (e.g. writes, in the header region of the image data in DICOM), information such as an ID to identify the dynamic image, the patient information, the examination information, the radiation emission conditions, the image reading conditions, and the respective numbers indicating what number in the imaging order the respective frame images have been taken (frame numbers), and sends the same to the diagnostic console 3 through the communication unit 25 (Step S8), and then ends the imaging control process. Then, the process ends. On the other hand, when the determination result "Imaging NG" is input by the radiographer performing a predetermined operation on the operation interface 23 (Step S7; NO), the controller 21 deletes the frame images (the series of frame images) from the storage 22 (Step S9), and then ends the imaging control process. In this case, re-imaging is necessary.

(Actions of Diagnostic Console 3)

Next, actions of the diagnostic console 3 are described.

Figure 3:
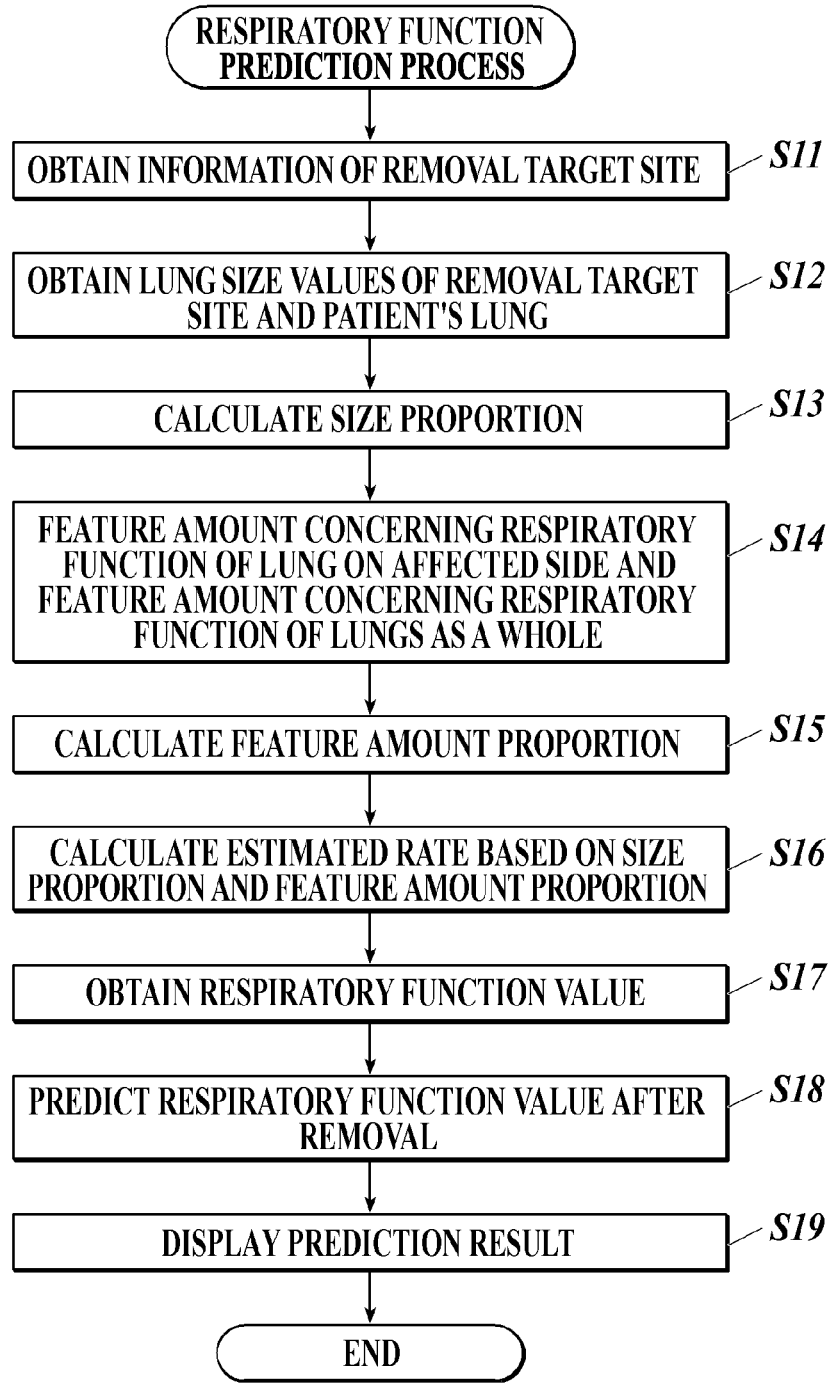
FIG. 3 is a flowchart of respiratory function prediction process executed by a controller of a diagnostic console shown in FIG. 1 according to the first embodiment.

In the diagnostic console 3, when receiving a series of frame images of a dynamic image of the chest from the imaging console 2 through the communication unit 35, the controller 31 performs the respiratory function prediction process shown in FIG. 3 in cooperation with the program stored in the storage 32. The respiratory function prediction process is to predict the respiratory function after the pulmonary excision surgery. Hereinafter, the respiratory function prediction process is described with reference to FIG. 3.

First, information on the removal target site which is to be removed from the lung field by excision surgery is obtained (Step S11).

Partial excision of the lung is performed in anatomical unit of the lung. The anatomical units of the lungs are left/right lungs, lobes, pulmonary segments, pulmonary subsegments, etc., in descending order. FIG. 4 shows anatomical units of the lungs (left/right lungs, lobes (right superior lobe, middle lobe, right inferior lobe, etc.), pulmonary segments (S1+2, S3, S4, etc.). The pulmonary segments are subdivided into the pulmonary subsegments.

Partial excision of the lung is commonly performed by unit of lobe, but in a case where limited surgery is necessary, it is performed by unit of pulmonary segment or subsegment. The entire right or left lung is sometimes excised. At Step S11, for example, the anatomical units of the lungs may be listed on the display 34, and an anatomical unit of the lungs selected by a mouse or the like of the operation interface 33 may be obtained as information on the removal target site. Alternatively, an anatomical unit of the lungs input by the user using a keyboard or the like of the operation interface 33 may be obtained as the information on the removal target site. Alternatively, the information on the removal target site in the lung field of the subject M may be obtained from the information stored in the memory of the electronic medical record system (e.g., electronic medical record information) via the communication unit 35.

Then, the lung size value of the removal target site and the lung size value of the lung on the affected side are obtained (Step S12).

The lung on the affected side means a left or right lung with a lesion, that is, with the removal target site.

The lung size value means a value representing the size in proportion to the lung fields as a whole (e.g., a value specifying the proportion (%) to the volume of the entire lung field).

At Step S12, for example, the table of lung size values 321 shown in FIG. 5 is referred to, and the lung size value corresponding to the anatomical unit of the removal target site is obtained. In FIG. 5, the lung size values are shown for 19 pulmonary segments, which are presented in the guideline of the Japan Lung Cancer Society. The guideline presents the 19 lung segments. The left superior lobe shown in FIG. 4 is divided into three segments of "S1+2" and "S3" (the number of pulmonary segments: 3) among the 18 pulmonary segments, and one of those segments have the size of 1/19 of the lungs as a whole. Each lobe and the left/right lung is divided into plural pulmonary segments. The lung size value (the proportion (%) to the volume of the lungs as a whole) of the anatomical unit of the lobe or (left or right) lung as the removal target site can be specified by the number of the pulmonary segments included in the lobe or left/right lung.

In FIG. 5, the number of the pulmonary segments by each anatomical unit is presented as the lung size value while the number of the pulmonary segments is 19, as shown in the guideline of the Japan Lung Cancer Society. But the lung size value is not limited to the number of the pulmonary segments presented in that guideline. Other values are applicable as long as they accurately represent the size in proportion to the lungs as a whole (e.g., a value that can specify the proportion (%) to the volume of the lungs as a whole). For example, the lung size value of each anatomical unit may be specified by the number of the lung segments as the lungs are divided into 22 segments. Alternatively, the number of the pulmonary subsegments may be the lung size value.

The volume of the lung on the affected side or the anatomical unit corresponding to the removal target site which is accurately measured for each patient using images taken by CT (Computed Tomography) or the like may be used to specify the lung size value, instead of using the table of lung size values 321.

This makes it possible to obtain a more accurate lung size value. In a case where CT images are used, emphysema may be taken into consideration, for example, and a part with a CT count value smaller than a predetermined reference value in the CT images may be excluded from the lung volume as emphysema site. The CT images may be used to modify the lung size value of the lung on the affected side or the removal target site obtained by the table of lung size values 321 suitably for each patient.

Next, the proportion of the lung size value of the removal target site and the lung on the affected side (Formula 1) is calculated as a size proportion (Step S13).

The size proportion=the lung size value of the removal target site/the lung size value of the lung on the affected side  (Formula 1)

Next, feature amounts of the respiratory function of the lung on the affected side and the lung fields as a whole are calculated (Step S14).

The feature amount of the respiratory function of the lung on the affected side is: a feature of the respiratory function of the left lung if the affected site is in the left lung; and a feature amount of the respiratory function of the right lung if the affected site is in the right lung. The feature amount of the respiratory function of the lung fields as a whole is the sum of the feature amounts of the respiratory function of the left lung and the right lung.

The feature amount of the respiratory function may be based on blood flow, ventilation, or a combination thereof (a feature amount VQ). The blood flow is usually reduced in a region of the lung where the ventilatory function deteriorates. Accordingly, the regional distribution of ventilation can be inferred from either the blood flow feature amount or the ventilation feature amount. However, soon after ventilatory impairment arises, the blood flow may be still observed in a region where the ventilatory function deteriorates. The blood flow may be absent while the ventilation is functioning in some region due to pulmonary embolism or the like. The respiratory function cannot be assured unless both the blood flow and the ventilation are functioning. Thus, the respiratory function after surgery can be predicted more accurately using the feature amount VQ that is based on the ventilation and the blood flow instead of using either the ventilation feature amount or the blood flow feature amount individually.

<Blood Flow Feature Amount>

The blood flow feature amount can be calculated, for example, by the following Steps I to VIII.

I. First, a frame image taken in a breath holding state from a series of the received frame images.

For example, the average pixel value of the entire image is calculated for each of the frame images. Then, if absolute values of difference between adjacent frame images are below a predetermined threshold value in continuous frame images, the section with the said continuous frame images are obtained as the frame images taken in a breath holding state.

The frame image to be obtained may be taken in a quiet inspiration/expiration state or in a deep inspiration/expiration state, and may be taken in a standing position, in a lying position, or in a sitting position.

II. The lung field region (right lung field region, left lung field region) is automatically extracted from each of the obtained frame images.

Figure 6:
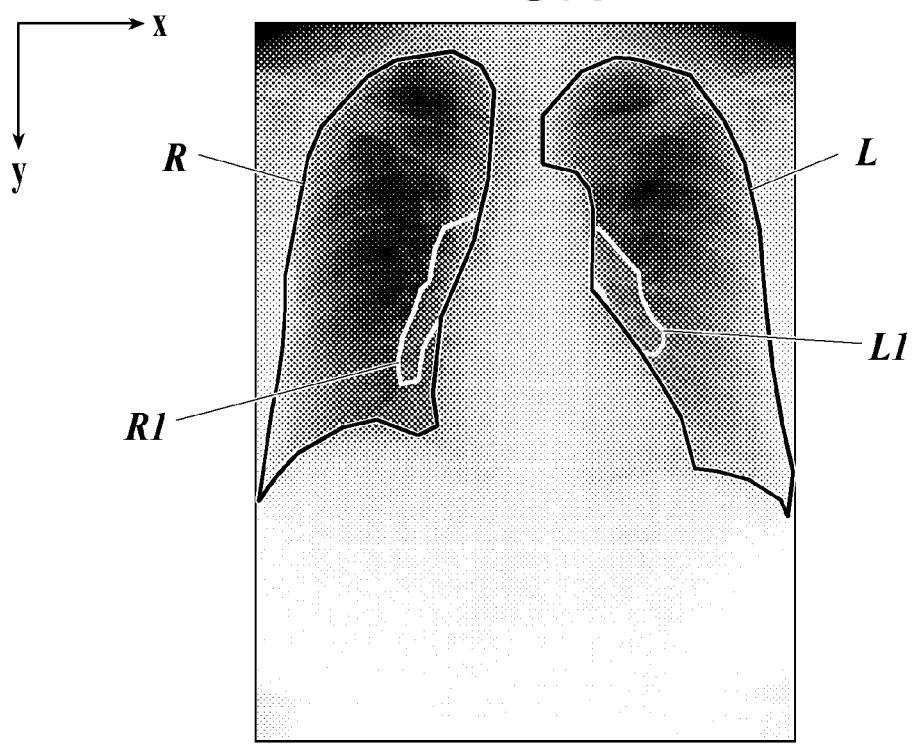
FIG. 6 shows regions of the lung fields and lung lobes.

Any lung field region extraction method can be used. For example, a threshold value is obtained from a histogram of pixel signal values (density values) of frame images by discriminant analysis, and a region having a higher signal values equal to or larger than the threshold value is primarily extracted as a lung field region candidate. Then, edge detection is performed around the border of the primarily extracted lung field region candidate, and, in small blocks around the border, points where the edge is the maximum are extracted along the border, so that the border of the lung field region (right lung field region, left lung field region) can be extracted. FIG. 6 shows an example of the automatically extracted lung field region (right lung field region R, left lung field region L).

Though the lung parenchyma is present in the regions overlapping the mediastinum or the diaphragm three-dimensionally, the regions overlapping the mediastinum or the diaphragm are preferably excluded from the lung field region because the motion of diaphragm in pulsation causes large noise. The heart, aorta, and the like are desirably excluded from the region because those organs have many signals of blood flow other than those of the pulmonary blood flow.

In a case where a blocking process is later performed, a half of a block size (5.0 mm if the block size is 10 mm) of the boundary region from the edge of the extracted lung field region toward the inner side of the lung field that includes signal components of the outside of the lung field is preferably excluded from the lung field region. The feature amount of blood flow may be calculated without the blocking process, and in that case, the feature amount can be calculated largely including the boundary of the lung field without the procedure described above.

The boundary of the outer rib cage is preferably excluded from the lung field region, because, in that region, a little motion of body causes a lot of noise, making the signal-noise ratio (S/N) poor. In a case where the feature amount of blood flow is to be calculated, the peripheral lung field may be excluded without much impact, because the amount of blood flow affected by pulsation is small in the peripheral lung field. The exclusion range may be a fixed range, for example, of 1 cm from the boundary of the lung field in the horizontal direction (x direction). Alternatively, the exclusion range may be determined by image analysis. The exclusion range may be determined and excluded as follows: obtaining the pixel value profile in the x direction (because motion of body causes more noise in the region where the pixel values largely differ in the x direction (left-right direction) of the image); checking the inclination of the profile from the boundary region of the outer rib toward the inner side of the lung field; detecting sections where the inclination is equal to or smaller than a predetermined value; determining the range between the boundary of the outer rib cage and the sections where the inclination is smaller than the predetermined value as a range where motion of body easily causes noise; and excluding the said range.

In a case where the feature amount of blood flow is calculated, only the lobe region among the lung field region (right lung field region, left lung field region) may be a target of the feature amount of the lung field as shown as R1 and L1 in FIG. 6. The lobe is approximately at the center of the lung where the bronchi, arteries, and veins enter and leave the lung. That is, the lobe, which is at the starting position of blood vessel running of the lung field, has a large amount of blood flow, and the lung vessels extend from the lobe toward the outer contour of the lung field.

A lung vessel region having a diameter of equal to or greater than 1 cm is extracted to detect the lobe region, for example. The lobe region may be extracted using a line detecting filter targeting at lines having a diameter of equal to or greater than 1 cm.

Furthermore, the frame image onto which the contour of the lung field automatically extracted by the above method is added may be displayed on the display 34 and manually adjusted by the user via the operation interface 33.

III. The extracted lung field region on each frame image is processed by blocking, logarithmic conversion, and the like.

In the blocking process, a pixel value of a pixel is substituted by the reference value (average value, etc.) of pixel values in a small block (rectangle of 10 mm) including the said pixel, and white noise and motion effects can be reduced.

The logarithmic conversion allows measurement of change in substance thickness over time.

Such processes are desirable but may be omitted.

IV. A waveform of each of pixel values that changes over is obtained in the lung field and processed with a high-pass filter (ex. 0.8 Hz), a band-pass filter (cardiac cycle), or the like in the time-axis direction.

This can reduce effects of body motions, or the like.

V. A frame image corresponding to the heart in the ventricular end-diastolic period is set as a reference frame image.

Specifically, the ventricle region of the heart in each frame image is set as a region of interest (ROI), and the frame image having the smallest density value (pixel value) in the region of interest (ROI) is set as the reference frame image.

The smallest density value indicates that the blood amount is the largest there in the ventricle region that is set as the region of interest (ROI).

Figure 7:
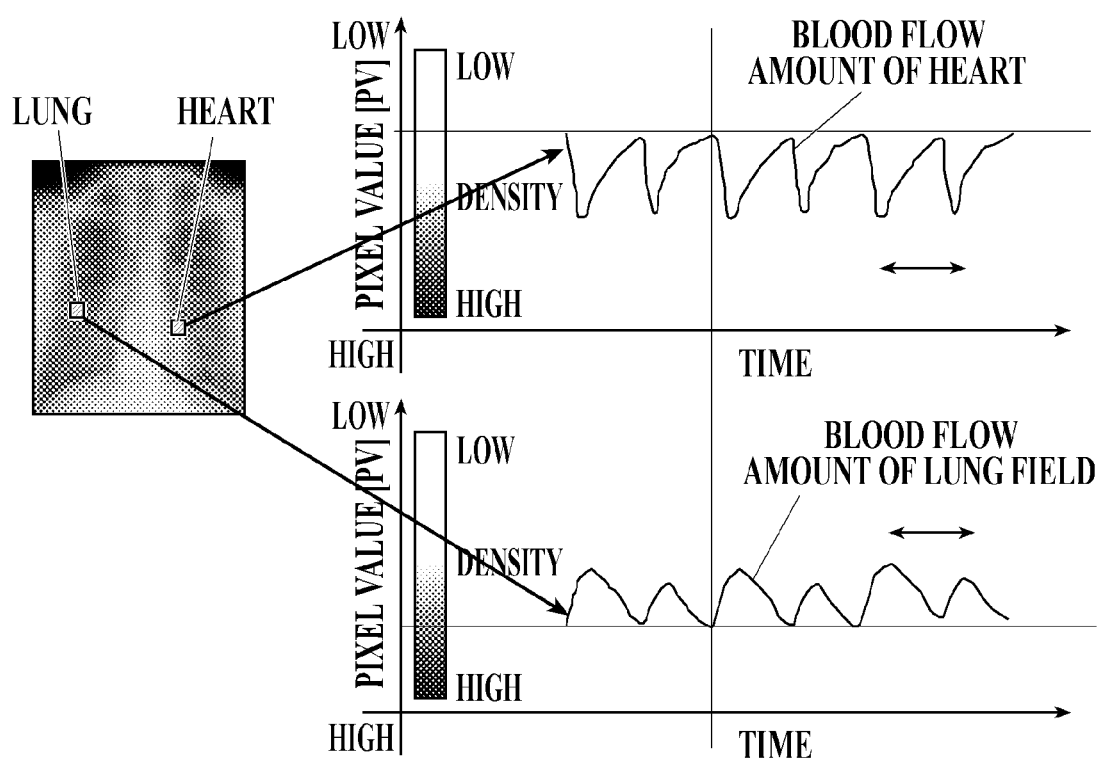
FIG. 7 shows two graphs in which the blood flow amount of the heart on the upper graph and the blood flow amount of the lung field on the lower graph.

FIG. 7 shows two graphs in which the blood flow amount of the heart on the upper graph and the blood flow amount of the lung field on the lower graph. In each graph of FIG. 7, the pixel values are shown in the vertical axis with the density of shading.

Blood flow into organs impedes transmission of radiation and reduces the transmission amount of radiation in radiographic images. Accordingly, regions of blood flow have smaller pixel values and are whitened (that is, in a lower density) on the radiographic images. In the light of the relation between the vascular blood flow that flows into and out of the lung field and the cardiac blood flow that flows into and out of the heart, when a lot of blood is flowing into the heart in the ventricular diastolic period, the transmission of radiation is impeded in the heart region, and accordingly, the heart region have smaller pixel values and is rather whitened (that is, in a lower density) on the radiographic images, as shown in FIG. 7. On the contrary, a little blood flows into the lung field at this timing, and transmission of radiation increases in the lung field. Accordingly, the lung field region has larger pixel values and is rather dark (that is, in a higher density) on the radiographic images. When blood flows out of the heart in the ventricular systolic period, the transmission amount of radiation is larger in the heart region, and accordingly, the heart region have larger pixel values and is rather dark (in a higher density) on the radiographic images. On the contrary, a lot of blood flows into the lung field at this timing, and transmission of radiation is impeded in the lung field. Accordingly, the lung field region has smaller pixel values and is rather whitened (that is, in a lower density) on the radiographic images.

VI. For each pixel of the extracted lung field region of each frame image, a differential value (an amount of density change from the reference frame image) between the pixel and the corresponding pixel (the pixel at the same location) of the reference frame image is calculated. This makes the feature amount of blood flow of each pixel.

VII. The total of the feature amounts of blood flow in all the pixels in the lung field region calculated in the Step VI is calculated as the feature amount of blood flow of the lung fields as a whole. The total of the feature amounts of blood flow in all the pixels in the right lung of the lung field region is calculated as the feature amount of blood flow of the right lung. The total of the feature amounts of blood flow in all the pixels in the left lung of the lung field regions is calculated as the feature amount of blood flow of the left lung.

VIII. The frame image having the smallest feature amount of blood flow of the lung fields as a whole is set as the representative frame image, and the feature amount of the blood flow of the representative frame image is set as the feature amount concerning the respiratory function.

The frame image having the smallest feature amount of blood flow of the lung fields as a whole, which has a high signal-noise ratio (S/N) showing the largest feature amount of blood flow in the lung field region, is appropriate for the representative frame image. However, the feature amount concerning the respiratory function is not limited to the feature amount of blood flow of the representative frame image, and may be the sum of the feature amounts of blood flow of multiple frame images, for example, in one heartbeat. Other methods may also be employed.

<Feature Amount of Ventilation 1>

The feature amount of ventilation can be calculated, for example, by the following Steps I to VIII.

I. First, a frame image taken in a breathing state from a series of the received frame images.

For example, the average pixel value of the entire image is calculated for each of the frame images, and a section of frame images that have an amplitude of a waveform showing change of the average pixel value over time larger than a predetermined threshold value is obtained as the frame images taken in the respiration state.

The frame image to be obtained may be taken in a quiet respiration state or in a deep respiration state, and may be taken in a standing position, in a lying position, or in a sitting position.

II. The lung field region is extracted from each of the extracted frame images.

The method of extracting the lung field region is described above. The expansion degree of the lungs changes for each frame image with breathing. The location deviation of the lung field region may be corrected by known local matching and image warping (ex. JP2012-005729A).

III. The extracted lung field region on each frame image is processed by blocking, logarithmic conversion, and the like.

Such processes are desirable but may be omitted.

IV. A waveform of each pixel value that changes over time is obtained in the lung field and processed with a high-pass filter (ex. 0.8 Hz) or the like in the time-axis direction.

This can reduce white noise and motion effects.

V. A frame image taken in the expiration state is set as a reference frame image.

For example, the location of the diaphragm on each frame image is automatically extracted by template matching or the like, and the frame image at the timing when the diaphragm is the closest to the apex of the lung is extracted as the frame image taken in the expiration state. Other methods may also be employed.

VI. The frame image in the inspiration state is set as the representative frame image.

For example, the location of the diaphragm on each frame image is automatically extracted by template matching or the like, and the frame image at the timing when the diaphragm is the furthest to the apex of the lung is extracted as the frame image taken in the inhalation state. Other methods may also be employed.

VII. For each pixel of the lung field region of the representative frame image, a differential value (a change amount of density from the reference frame image) between the pixel and the corresponding pixel (the pixel at the same location) of the reference frame image is calculated. This makes the feature amount of ventilation of each pixel.

VIII. The total of the feature amounts of ventilation in all the pixels in the lung field region calculated in the Step VII is calculated as the feature amount of ventilation of the entire lung field. The total of the feature amounts of ventilation in all the pixels in the right lung of the lung field region is calculated as the feature amount of ventilation of the right lung. The total of the feature amounts of ventilation in all the pixels in the left lung of the lung field regions is calculated as the feature amount of ventilation of the left lung.

As the expansion degree of the lung changes with respiration, the density also changes. Thus, the feature amount of ventilation may be extracted by measurement of the density of the lung vessels. For example, the method may be as follows: (two or more) feature points (ex. bifurcation point of lung vessel) are detected on an image; the movements of the feature points are tracked by template matching or the like and measured; the change amount of the distance between the feature points on the representative frame image and the change amount of the distance of the feature points on the reference frame image are measured and determined as the feature amount of ventilation.

<VQ Feature Amount>

The feature amount of VQ can be calculated, for example, by the following Steps I to III.

I. The left-right ratio of the feature amounts of ventilation and blood flow.

II. A representative value of the values of the right of the left-right ratios of the feature amounts of ventilation and blood flow obtained in Step I is obtained as VQ'(R). For example, if the left-right ratio of the feature amount of ventilation is 5:5 (right:left) and the left-right ratio of the feature amount of blood flow is 7:3 (right:left), the value of the right of the feature amount of ventilation is 5 and that of blood flow is 7. If the representative value is the minimum value, VQ'(R)=5 in this case. The obtained VQ'(R) is defined as the feature amount of ventilation of the right lung. Similarly, a representative value of the values of the left of the left-right ratios of the feature amounts of ventilation and that of blood flow obtained at the Step I is obtained as VQ'(L). The obtained VQ'(L) is defined as the feature amount of ventilation of the left lung.

III. VQ'(R)+VQ'(L) is defined as the feature amount of the lungs as a whole.

The representative value may be the minimum, maximum, average, or median value. Alternatively, the representative value may be the sum or the product of the values of the right of the feature amounts of ventilation and blood flow. The minimum value is preferable because the feature amount of the less functional one of ventilation and blood flow can be reflected on the expected rate.

After the feature amounts are calculated, the proportion of the feature amounts of the lung on the affected side and the entire lung field concerning the respiratory function is calculated as the feature amount proportion (Step S15). The feature amount proportion is a contribution proportion of the lung on the affected side to the overall respiration.

Then, on the basis of the size proportion and the feature amount proportion calculated, the expected rate to predict the respiratory function value after excision of the removal target site from the entire lung field is calculated (Step S16).

The expected rate can be obtained by the following Formula 2.

$$\text{The expected rate} = 1 - \text{the feature amount proportion} \times \text{the size proportion} \quad \text{(Formula 2)}$$

The feature amounts of blood flow, ventilation, and VQ described above are examples of the feature amount concerning the respiratory function, and feature amounts obtained by other method may be employed.

Next, the respiratory function value of the subject is obtained (Step S17).

A value measured by a spirometry test, for example, may be obtained as the respiratory function value. Though % FEV1 is listed as the respiratory function value used to calculate the risk of lung cancer surgery in the guideline of the Japan Lung Cancer Society, other respiratory function values may be obtained. For example, FEV1, VC, % VC, FVC, % FVC, FEV1%, % FEV1% may be used.

The respiratory function value may be estimated from a dynamic or still image(s). For example, the ventilation amount can be estimated by the difference between the lung field areas on the frame images taken in the expiration state (maximum expiration state) and in the inspiration state (maximum inspiration state) in deep breathing. The image(s) used in this process may be the front view or lateral view, and the accuracy is improved if the ventilation amount is estimated by the lung field volume that is calculated using both of them. The difference between the lung field areas on the frame images taken in the inspiration and expiration states in a quite respiration or in an effort respiration may be calculated. Alternatively, the ventilation amount may be calculated using the difference in the lung field areas in one minute similarly to FEV1.

An image taken only in the expiration state or inspiration state may be used for the still image, and the ventilation amount may be estimated similarly using an image taken in the inspiration state and an image taken in the first minute of expiration for FEV1. Alternatively, the ventilation amount may be estimated by the movement amount of the diaphragm instead of the entire lung field.

Use of a spirometer puts high burden on patients in measurement of the respiratory function values. Measurement of the respiratory function values on the basis of the dynamic images can reduce burden on patients and facilitate the examination.

Next, the respiratory function value after surgery (the respiratory function value after the removal target site is removed from the lung field) is predicted on the basis of the expected rate calculated at Step S16 (Step S18).

The respiratory function value after surgery can be predicted by following Formula 3.

The respiratory function value=the respiratory function value×the expected rate   (Formula 3)

Then, the predicted respiratory function value after surgery is displayed on the display 34 (Step S19), and the respiratory function value prediction process is completed.

The order relation of Steps S11 to S19 of the respiratory function prediction process is not limited to the example described above. For example, Step S17 may be performed before Step S11, or Steps S12 and S13 may be switched with Step S14 and s15. Other replacements of the order are also possible.

As described hereinbefore, the controller 31 of the diagnostic console 3, in receipt of information on the removal target site in the lung fields, obtains the lung size value of the removal target site and the lung size value of the left or right lung field that includes the removal target site, in lung fields, and calculates a proportion between the lung size value of the removal target site and the lung size value of the left or right lung field that includes the removal target site, as a size proportion. The controller 31 then calculates the feature amount concerning respiratory function of the left or right lung field that includes the removal target site and the feature amount concerning respiratory function of the lung fields as a whole based on the plurality of frame images of the dynamic image of the chest, and calculates a proportion between the feature amount concerning the respiratory function of the left or right lung field that includes the removal target site and the feature amount concerning the respiratory function of the lung fields as a whole, as a feature amount proportion. The controller 31 then calculates an expected rate of the respiratory function after the removal target site is removed from the lung fields, based on a product of the calculated size proportion and the calculated feature amount proportion.

Thus, the expected rate of the respiratory function can be calculated on the two-dimensional dynamic image without specifying the region of the removal target site according to the present invention unlike the prior art. This enables accurate calculation of the expected rate of the respiratory function value used for prediction of the respiratory function value after surgery.

For example, the controller 31 obtains, from the storage 32 in which lung size values of anatomical units of lungs are stored, the lung size value of the anatomical unit corresponding to the removal target site and the lung size value of an anatomical unit corresponding to the left or right lung field that includes the removal target site. This enables determination of the lung size of the removal target site without specifying the region of the removal target site on the two-dimensional dynamic image.

The controller 31 also obtains the respiratory function value of the lung fields as a whole of the subject, and multiplies the obtained respiratory function value by the expected rate to obtain the expected respiratory function value after the removal target site is removed from the lung fields. This enables prediction of the respiratory function value after the removal target site is removed from the lung field.

The expected rate is determined using the dynamic image (s) taken before the lung surgery. The target site is a target site to be removed in the lung surgery. The expected rate of the respiratory function value after the lung excision can be calculated by the process described above.

The controller 31 automatically extracts left and right lung field regions from the frame images of the dynamic image, and calculates the first feature amount concerning the respiratory function of the left or right lung field that includes the removal target site and the second feature amount concerning the respiratory function of the lung fields as a whole, based on the left and right lung field regions extracted from the plurality of frame images. This enables accurate calculation of the expected rate while the user do not need to specify the lung field region on the dynamic image.

Apart from the method according to the present embodiment, one of the methods for predicting the respiratory function after surgery is a pulmonary blood flow scintigraphy test. However, the pulmonary blood flow scintigraphy test requires a huge and expensive test equipment. Only comparatively large hospitals can own such an equipment, and otherwise it cannot be used. Even in a medical facility with a scintigraphy test equipment, the patients usually have to be on a one-week waiting list for a scintigraphy test after ordering because of necessity for management of radioisotopes, and are subject to large exposure. Thus, only patients with high risk undergo a scintigraphy test.

Risk of complications is not accurately comprehended in many cases because of this problem.

At least, the lung field region need to be located based on the image to calculate the expected rate of the respiratory function value from the image. However, the pulmonary blood flow scintigraphy test just gives images of blood flow of the left and right lung, and it is impossible to accurately figure out where the lung field region is. The lung field region need to be set manually by a doctor at their own responsibility, and the expected rate cannot be accurately calculated in spite of time it takes.

However, according to the method in the present embodiment, the contour of the lung field region can be spotted using the dynamic image that reflects the radiography of the chest and the expected rate of the respiratory function value can be accurately calculated. Also, the doctors do not have to take time to manually set the lung field region. In the case where the respiratory function value is predicted from images obtained by the pulmonary blood vessel scintigraphy test, it is necessary to average values using images taken in two directions of anterior (ANT) and posterior (POST). In the case where the dynamic image is used, it is only necessary to analyze an image(s) taken in one direction (ex. ANT), which reduces processing time.

Accordingly, according to the present embodiment, the expected rate after the removal target site is removed can be calculated on the basis of the dynamic images taken by the radiographic imaging apparatus which a wide-range of medical facilities can own. It does not necessitate its users spotting the range of the removal target site on two-dimensional images and reduces stress on patients.

The embodiments described above are merely preferable examples, and the embodiments are not limited to the above.

For example, in the embodiments described above, the respiratory function after surgery is predicted in the case where a part of the lung is excised by surgery and the respiratory function of the part is removed. However, the present invention can be applied to prediction of the respiratory function after surgery in the case where the respiratory function of a part is removed by radiation therapy or laser irradiation instead of excision.

In the embodiments described above, the information on the anatomical unit of the removal target site is obtained by input via the operation interface 33, and the lung size values of the removal target site and the left or right lung field that includes the removal target site is obtained on the basis of the obtained information on the anatomical unit of the removal target site. However, the lung size values of the removal target site and the lung field that includes the removal target site may be directly obtained. For example, a volume of the removal target site that is obtained by a CT scan result or the like may be obtained as the lung size volume pf the removal target site, and a volume of the lung field that includes the affected side as the lung size value of the lung field that includes the affected side, by input by the user via the operation interface 33.

The above description discloses an example of using a hard disk, a semiconductor nonvolatile memory and the like as the computer readable medium of the program according to the present invention. However the present invention is not limited to the example. A portable recording medium such as a CD-ROM can be applied as other computer readable mediums. A carrier wave is also applied as a medium providing the program data according to the present invention via a communication line.

While the present invention is described with some embodiments, the scope of the present invention is not limited to the above-described embodiment but encompasses the scope of the invention recited in the claims and the equivalent thereof.

Although embodiments of the present invention have been described and illustrated in detail, the disclosed embodiments are made for purposes of illustration and example only and not limitation. The scope of the present invention should be interpreted by terms of the appended claims

What is claimed is:

1. A dynamic analysis apparatus that predicts a respiratory function value of a subject based on a plurality of frame images showing dynamics of a chest of the subject, the dynamic analysis apparatus comprising: a hardware processor that:
    obtains a first lung size value of a removal target site and a second lung size value of a left or right lung field that includes the removal target site, in lung fields of the subject;
    calculates a proportion between the first lung size value of the removal target site and the second lung size value of the left or right lung field that includes the removal target site, as a size proportion;
    calculates a first feature amount concerning respiratory function of the left or right lung field that includes the removal target site and a second feature amount concerning respiratory function of the lung fields as a whole, based on the plurality of frame images;
    calculates a proportion between the first feature amount concerning the respiratory function of the left or right lung field that includes the removal target site and the second feature amount concerning the respiratory function of the lung fields as a whole, as a feature amount proportion; and
    calculates an expected rate of the respiratory function after the removal target site is removed from the lung fields, based on a product of the calculated size proportion and the calculated feature amount proportion.

2. The dynamic analysis apparatus according to claim 1, wherein the hardware processor:
    obtains information on an anatomical unit corresponding to the removal target site; and
    obtains, from a memory in which lung size values of anatomical units of lungs are stored, a lung size value of the anatomical unit corresponding to the removal target site and a lung size value of an anatomical unit corresponding to the left or right lung field that includes the removal target site.

3. The dynamic analysis apparatus according to claim 2, wherein each anatomical unit is any one of a left or right lung, a lobe, a pulmonary segment, and a pulmonary sub-segment.

4. The dynamic analysis apparatus according to claim 1, wherein the hardware processor:
    obtains a respiratory function value of the lung fields as a whole of the subject; and
    multiplies the obtained respiratory function value by the expected rate to obtain an expected respiratory function value after the removal target site is removed from the lung fields.

5. The dynamic analysis apparatus according to claim 1, wherein the plurality of frame images is images that are captured before lung surgery,
    wherein the removal target site is a target site to be removed in the lung surgery.

6. The dynamic analysis apparatus according to claim 1, wherein the first feature amount and the second feature amount are feature amounts of ventilation, feature amounts of pulmonary blood flow function, or feature amounts calculated respectively based on the feature amounts of ventilation and the feature amounts of pulmonary blood flow function.

7. The dynamic analysis apparatus according to claim 1, wherein the hardware processor:
    extracts left and right lung field regions from the plurality of frame images; and calculates the first feature amount concerning the respiratory function of the left or right lung field that includes the removal target site and the second feature amount concerning the respiratory function of the lung fields as a whole, based on the left and right lung field regions extracted from the plurality of frame images.

8. A dynamic analysis system comprising:
the dynamic analysis apparatus according to claim 1; and
an imaging apparatus that performs radiographic imaging of the subject to obtain the plurality of frame images showing dynamics of the chest of the subject.

9. An expected rate calculation method for a dynamic analysis apparatus that predicts a respiratory function value of a subject based on a plurality of frame images showing dynamics of a chest of the subject, the method comprising:
obtaining a first lung size value of a removal target site and a second lung size value of a left or right lung field that includes the removal target site, in lung fields of the subject;
calculating a proportion between the first lung size value of the removal target site and the second lung size value of the left or right lung field that includes the removal target site, as a size proportion;
calculating a first feature amount concerning respiratory function of the left or right lung field that includes the removal target site and a second feature amount concerning respiratory function of the lung fields as a whole, based on the plurality of frame images;
calculating a proportion between the first feature amount concerning the respiratory function of the left or right lung field that includes the removal target site and the second feature amount concerning the respiratory function of the lung fields as a whole, as a feature amount proportion; and
calculating an expected rate of the respiratory function after the removal target site is removed from the lung fields, based on a product of the calculated size proportion and the calculated feature amount proportion.

10. A non-transitory recording medium storing a computer-readable program that causes a computer used for a dynamic analysis apparatus that predicts a respiratory function value of a subject based on a plurality of frame images showing dynamics of a chest of the subject:
to obtain a first lung size value of a removal target site and a second lung size value of a left or right lung field that includes the removal target site, in lung fields of the subject;
to calculate a proportion between the first lung size value of the removal target site and the second lung size value of the left or right lung field that includes the removal target site, as a size proportion;
to calculate a first feature amount concerning respiratory function of the left or right lung field that includes the removal target site and a second feature amount concerning respiratory function of the lung fields as a whole, based on the plurality of frame images;
to calculate a proportion between the first feature amount concerning the respiratory function of the left or right lung field that includes the removal target site and the second feature amount concerning the respiratory function of the lung fields as a whole, as a feature amount proportion; and
to calculate an expected rate of the respiratory function after the removal target site is removed from the lung fields, based on a product of the calculated size proportion and the calculated feature amount proportion.

\* \* \* \* \*